United States Patent [19]

Drost

[11] Patent Number: 4,550,606
[45] Date of Patent: Nov. 5, 1985

[54] ULTRASONIC TRANSDUCER ARRAY WITH CONTROLLED EXCITATION PATTERN

[75] Inventor: Cornelis J. Drost, Ithaca, N.Y.
[73] Assignee: Cornell Research Foundation, Inc., Ithaca, N.Y.
[21] Appl. No.: 425,798
[22] Filed: Sep. 28, 1982
[51] Int. Cl.⁴ ............................................. G01N 29/00
[52] U.S. Cl. ...................................... 73/626; 73/628; 367/105; 310/334; 310/336; 128/660
[58] Field of Search .................... 73/625, 626, 628; 367/105, 103, 62; 310/334, 336, 363; 128/660

[56] References Cited

U.S. PATENT DOCUMENTS

| | | | |
|---|---|---|---|
| 2,698,927 | 1/1955 | Parr, Jr. ............................... | 367/62 |
| 2,928,068 | 3/1960 | Samsel et al. ...................... | 310/334 |
| 3,096,846 | 7/1963 | Savit et al. ......................... | 367/62 |
| 3,820,387 | 6/1974 | Grabendorfer et al. | |
| 3,824,531 | 7/1974 | Walsh . | |
| 3,836,948 | 9/1974 | Burkhardt et al. | |
| 3,881,466 | 5/1975 | Wilcox . | |
| 3,911,730 | 10/1975 | Niklas . | |
| 3,979,711 | 9/1976 | Maginness et al. ................. | 340/105 |
| 4,101,795 | 7/1978 | Fukomoto et al. ................. | 310/336 |
| 4,106,348 | 8/1978 | Auphan ................................ | 73/624 |
| 4,112,411 | 9/1978 | Alais et al. ........................... | 73/626 |
| 4,117,446 | 9/1978 | Alais .................................... | 73/607 |
| 4,140,022 | 2/1979 | Maslak ................................ | 73/626 |
| 4,145,931 | 3/1979 | Tancrell .............................. | 73/626 |
| 4,180,792 | 12/1979 | Ledernian et al. ................. | 73/626 |
| 4,192,977 | 3/1980 | Stamm ................................ | 73/632 |
| 4,219,846 | 8/1980 | Auphan ................................ | 73/626 |
| 4,241,610 | 12/1980 | Anderson ............................ | 73/626 |
| 4,277,712 | 7/1981 | Hanafy ................................ | 73/632 |
| 4,281,550 | 8/1981 | Erikson ................................ | 73/626 |
| 4,287,770 | 9/1981 | Weyns ................................. | 73/632 |
| 4,446,396 | 5/1984 | Claus et al. ......................... | 310/334 |

OTHER PUBLICATIONS

J. Meindl and A. Macovski, "Recent Advances in the Development of New Imaging Techniques", Stanford Elc. Labs., Chapt. 8, vol. 1, 175–201.
N. Born, F. Hagemeijer, C. T. Nacee, J. Roelandt, C. Ligtvoet and J. A. Vogel, Erasmus Univ., "Two-Dimensional Real-Time Echocardiography", Chapt. 9, Research Studies Press, 203–211 (1977).
F. D. Martin and M. A. Breadzeale, "A Simple Way to Eliminate Diffraction Lobes Emitted by Ultrasonic Transducers" Jor. Acoust. Soc.
M. A. Breazeale, F. D. Martin and Bruce Blackburn, "Reply to Radiation Pattern of Partically Electroded Piezoelectric Transducers" 70(6) 1791–1793 (1981).
J. Jarzynski and W. J. Trott, "Array Shading for a Broadband Constant Directivity Transducer" Jour. Acoustic Soc. 64(5) 1266–1269 (1978).
T. A. Whittingham, "A Hand-Held Electronically Switched Array for Rapid Ultrasonic Scanning", Ultrasonics 29–33 (1976).
L. Pourcelot, M. Berson and A. Roncin, "Use of a Liner Multitransducer Array for Real-Time Compound Scanning", Fifth International Symposium on Ultrasonic Imaging and Tissue Characterization, National Bureau of Standards, 66 (1980).
L. Filipczynski and J. Etienne, "Theoretical Study and Experiments on Spherical Focusing Transducers with Gaussian Surface Velocity Distribution", Acustica vol. 28, 121–138 (1973).
R. D. Selbie, J. M. S. Hutchison and J. R. Mallard, "The Aberdeen Phased Array: A Real-Time Ultrasonic Scanner with Dynamic Focus", Med. & Bio. Eng. & Comput., 18 335–343 (1980).
von K. von Haselberg and J. Krautkramer, "Ein Ultraschall-Strahler fur Die Werkstoffprufung mit Verbessertem Nahfeld", Acustica vol. 9, 359–364 (1959).

Primary Examiner—Howard A. Birmiel
Attorney, Agent, or Firm—Jones, Tullar & Cooper

[57] ABSTRACT

A transducer array and excitation circuitry for producing ultrasonic waves in a controlled pattern and for causing the waves to be scanned along the array. The array comprises a plurality of transducer elements coupled to each other in such a way as to produce a desired wave pattern when selected elements are activated. The array may be constructed from plural transducer elements or from a single plate of transducer material comprising a plurality of elements that can be individually activated, the plural elements being intercoupled to produce the desired wave pattern. The arrangement is such that a minimum number of electrical connections to the transducer elements are required to create the desired wave pattern and to scan that pattern across the face of the array.

33 Claims, 11 Drawing Figures

ULTRASONIC TRANSDUCER ARRAY WITH CONTROLLED EXCITATION PATTERN

The present invention was developed in the course of work done under NIH Grant No. HL-19019; accordingly, the U.S. government has rights in the invention.

BACKGROUND OF THE INVENTION

The present invention relates, in general, to a high resolution ultrasonic scanner, and more particularly to a transducer array producing an output acoustic wave pattern through the controlled excitation of the elements of the array. Most particularly, the invention is directed to biomedical transcutaneous B-scanning apparatus.

Existing B-scan probes, which are particularly useful in medical diagnostics, fall into two general categories, both of which utilize transducers capable of producing pressure waves which can be formed into a beam, the direction of which is changeable so as effectively to scan a sector. One category of probes includes those which employ a single beam transducer assembly wherein the beam can be steered either by mechanically moving the assembly or by controlling the phase of the electrical signals applied to the transducer elements to scan tissue under study. A second category includes probes which employ an array of transducer elements wherein the scanning motion is achieved by electronically addressing different portions of the array. In transducers of either category, pressure waves are radiated from the transducer elements and pass into and through tissues of interest, with a portion of the wave energy being reflected whenever the waves encounter an interface of tissues having different acoustic characteristics. The returned energy is directed to suitable receiving transducers which convert the reflected pressure waves into corresponding electrical signals for display, for example, on a cathode ray tube.

Transducers in the first category produce the best resolution of tissue configurations, since the transducer assembly can readily be optimized so that the field covered by its single beam is of the desired size for detecting specific features. However, such assemblies must either be mechanically driven for beam steering, or must utilize complex phasing networks to obtain the desired scanning motion of the beam, and such arrangements are complex and expensive. On the other hand, probes in the second category, employing an array of electronically scanned transducer elements, are simpler and considerably less expensive, although their resolution is inferior.

In its simplest form, an electronically scanned transducer array consists of a row of transducer elements. One element of this array is employed in an ultrasonic pulse-echo mode in order to measure acoustic reflections off tissue interfaces ahead of the transducer as a function of the distance from the transducer. This same procedure is repeated for all of the elements of the linear array and all of the individual lines of view are combined to provide a full picture, ideally showing the outlines of all acoustically different tissue interfaces in the object under study. In a phased transducer array, each element is individually connected to a transmitter and receiver, but adjustable delays are provided in each receiver channel in order to enhance the reception from a selected direction. By suitably controlling the time at which electrical drive signals are applied to each of the transducer elements and by controlling the adjustable delays of the separate receiver channels, the effective direction of the pressure wave beam can be steered to any desired angle within a fan-shaped sector. In practice, a plurality of radial lines within the sector are successively generated to sequentially scan the entire sector. A set of such lines is generated over a short period of time, and the received signals are displayed on a cathode ray tube to provide a visualization of the outline of the tissue interfaces which produce the received signals. This visualization is known as a B-mode display, wherein variations of the acoustical impedance of the tissues are translated into brightness variations on the cathode ray tube.

Obtaining a high resolution ultrasonic image for medical diagnostic purposes requires an ultrasonic transmit-receive system having a small focal spot-size over its entire field of view. Otherwise, acoustic reflections from different structures within the focal area can constructively and destructively interfere, producing "specle" in the ultrasonic image. Conventional transducers may also suffer from poor resolution at distances near the transducer surface (the so-called "near field"), caused by interference resulting from pathlength differences between the constituent parts of the ultrasonic beam. A further source of error results from side lobes of the ultrasonic transmit-receive system. Obviously, echoes from a weak sidelobe can obliterate the echoes from weakly reflective structures in the main beam.

Many transducer systems have been produced which have been able to improve the resolution of ultrasonic images, with a variety of approaches having been taken. In U.S. Pat. Nos. 4,106,348 to Auphan, 4,281,550 to Ericson, 3,911,730 to Niklas, and 3,881,466 to Wilcox, for example, a number of transducer elements are excited in common in order to produce a simple scanned line. Other patents, for example U.S. Pat. No. 3,820,387 to Grabendorfer, employ different sets of transducers for the transmit and receive function. Still others improve the resolution of the ultrasonic image at different distances by the provision of "dynamic focusing", whereby the number of transducers addressed is varied across the depth of a scanned line (see, for example, U.S. Pat. No. 4,241,610 to Anderson and the references cited therein. See also R. D. Selbie et al, "The Aberdeen Phased Array: A Real-Time Ultrasonic Scanner With Dynamic Focus", Medical and Biological Engineering and Computing, May 1980, pages 335–343).

U.S. Pat. No. 4,219,846 to Auphen suggests that image resolution can be obtained through the employment of concentric circles of rectangular matrix elements selected from a transducer array. However, exhaustive switching means are required to scan this concentric selection across the face of the transducer assembly. Other patents, such as U.S. Pat. Nos. 4,112,411 to Alais and 4,145,931 to Tancrell also utilize more than one element of the array to produce a single line of the B-scan picture, and add the capability to excite these different elements in differing amplitudes and phases. However, because of their high level of electronic complexity these systems are used mainly with steered-beam types of B-scanners.

It has now been found that the main characteristics needed for a high-resolution transmit-receive system for a B-scanner; that is, good focus over a large depth of view with no side lobes, can be attained with a transducer surface vibration pattern that has a peak amplitude at its center but which decays in amplitude toward the perimeter, generally in the well-known "bell" shape. A transducer excited in such a bell-shaped, or "Gaussian" vibration pattern produces a radiation pattern which has no near field on-axis intensity fluctuations and no side lobes. And, by laws of reciprocity, such a transducer also has the same directivity pattern in its receive mode; it is primarily sensitive to acoustic waves striking its surface in the axial direction, and also sensitive to on-axis reflections off interfaces in the near field region, without the usual near-field fluctuations.

A large number of transducer designs have been produced which are capable of approximating a "Gaussian" directivity pattern; however, such designs have not been useful in improving the resolution of an electronically scanned linear transducer array, since the directivity pattern of such devices is traditionally achieved by geometry-dependent means which cannot be scanned across the surface of an ultrasonic B-scan sensor.

Typical of the transducer designs which are capable of producing a "Gaussian", or bell-shaped radiation pattern is the transducer described in the paper entitled "Theoretical Study and Experiments on Spherical Focusing Transducers With Gaussian Surface Velocity Distribution" by L. Filipczynski et al, Acustica, Vol. 28, pages 121–128, 1973, wherein one electrode of the transducer is in the shape of a rosette so that the electrical excitation decreases towards the edges of the transducer. It is also possible to reduce the electrical excitation toward the edges of a transducer by employing a convex-shaped electrode which contacts the flat transducer surface only at its center, and which is spaced further away from the transducer as the distance off center increases. On a transducer having fully-plated electrodes, a similar effect can be produced by mechanical means aimed at reducing the vibrational output away from its center, either by varying the mechanical damping across the back side of the transducer, or by applying to its front face a layer of material having varying attenuation (von Haselburg et al Ein Ultraschall-Strahler für die Werkstoffprüfung mit Verbessertem Nahfeld. Acustica, 9:359–364, 1959).

An alternative transducer design uses a resistive plating instead of a conductive material as one of the electrodes, whereby the surface resistivity increases as the distance away from the center is increased. The electrical excitation is then applied to the center of the transducer (von Haselberg et al, ibid). Still another approach is to plate only a central part of the transducer, relying upon electrical and mechanical fringing effects to achieve a decaying excitation function toward the edges of the transducer element (M. A. Breazeale et al, "Reply to 'Radiation Pattern of Partially Electroded Piezoelectric Transducers'," J. Acoust. Soc. Am. 70(6): 1791–1793, 1981).

All of the foregoing techniques achieve a shaped acoustic field pattern by mechanical or geometric shaping of the electrode or the transducer material. In each case, only a single electrical signal connection is provided, and the desired field pattern is generated by features built into the transducer, rather than through the control of a large number of individual transducers. However, the geometry-dependent mechanical construction of such devices prevents effective linear scanning of the radiation pattern and thus prevents the effective use of a "Gaussian" or bell-shaped surface excitation function in a scanning probe device.

SUMMARY OF THE INVENTION

It is an object of this invention to improve the performance of electronically scanned linear arrays, without sacrificing their cost effectiveness.

It is an object of the present invention to provide a transducer array which can be activated by a predetermined surface excitation function to produce a desired radiation pattern, such as a first-order approximation of a "Gaussian" pattern, which can be scanned across the surface of the transducer by simple electronic controls.

It is a further object of the invention to provide simple matrix constructions for transducer arrays which minimize the number of electrical connections needed to produce and electrically scan a predetermined surface excitation function.

Briefly, the present invention is directed to the provision of a low-cost, high-resolution B-scanner probe which utilizes an array of transducer elements which are intercoupled. When the array is excited at one of its matrix elements, in a transmit mode of operation, a localized area around that element of the array will be energized in a predetermined surface displacement function. This displacement function results in the transducer array producing a corresponding radiated field pattern. In its receive-mode of operation, the array is similarly terminated by the electronic circuitry to favor the same surface vibration pattern and thus the same directivity pattern.

The predetermined surface function for the array can be obtained in a variety of ways. Generally, a transducer array consists of a plurality of transducer elements with each element having conductive electrodes on its front and rear surfaces. In the present invention, elements are electrically coupled to each other by suitable impedances (e.g., combinations of resistors, capacitors and inductors) connecting adjacent electrode surfaces of the elements. In the transmit mode, a drive signal is applied via an external electrical connection to the electrode of an element selected as the center of excitation, and that signal is also supplied to adjacent elements through the interconnecting electrical impedances and through mechanical coupling between adjacent elements, thereby supplying the same signal but at reduced amplitude to such adjacent elements. The reduced signal amplitudes produce correspondingly reduced surface excitations in such adjacent elements, with the elements most distant from the location where the drive source is applied having the lowest excitation level. By proper selection of the impedance values, the excitation function for the array can be selected to produce a desired radiation wave pattern.

In the receive mode of operation, the inverse process occurs. An acoustic wave exciting various elements of the array produces voltages at each of their electrodes. These voltages are summed by the network of impedances interconnecting the elements. By reciprocity, this results in the same directivity pattern as exists in the transmit mode of operation; only when a wave in the axial direction strikes the transducer, these contributions add up to a net received voltage at the electrode of the element selected by the transmit-receive electronic circuitry.

The transducer elements may be individual units mounted on a suitable base, or may be constructed from a single plate, or slab of transducer material. The single plate construction is preferred, and the present invention is directed to a variety of ways for obtaining plural transducer elements from a single piece of material, with the elements being interconnected to produce a "Gaussian" or other selected vibration function, so that the transducer array will have a predetermined directivity pattern. The transducer material may be a conventional piezoelectric crystal having conductive coatings on its upper and lower surfaces by means of which electrical drive pulses can be applied across the crystal to cause to produce mechanical vibrations in known manner. The electrical connections for the various impedance elements are also made to the conductive coating.

In a first embodiment of the invention, the transducer elements are formed on a strip of transducer material coated on its upper and lower surfaces with a layer of conductive material by cutting a plurality of parallel spaced grooves across the upper portion of the strip. The grooves extend through the conductive layer and at least partially through the piezoelectric crystal to divide the material into a plurality of side-by-side segments which form a linear array of transducer elements. In a second embodiment, a two dimensional array of elements may be made by cutting spaced, parallel grooves in both the X and Y directions on the top portion of the transducer material, producing a plurality of rectangular segments Which serve as transducer elements, and which form, in effect, a series of side-by-side linear arrays.

In each of the foregoing embodiments, all adjacent elements are electrically interconnected by suitable impedances. A drive signal is applied directly to a selected one of the elements and at the same time is applied through the interconnecting impedance network to each of the other elements of the array, thereby exciting all of the elements at the same time but with the signal amplitude decreasing with the distance from the selected element thereby to produce a desired radiation pattern. Switching means is provided to selectively and serially connect the drive signal source to different elements, for example to adjacent elements in a row, to scan the radiated signal. The signal thus applied is connected through suitable impedances to all of the remaining elements in the array as described, so that a multi-dimensional radiation pattern of desired shape can be scanned across the array by switching the excitation point from one element to the next.

In a third embodiment of the invention, the transducer elements of an array are formed in a single slab of transducer material by means of grooves cut partially through opposite sides of a conductively plated slab. On one side, equidistant parallel cuts are made in the X direction, forming therebetween the rows of a matrix of elements. The other side is formed with similar cuts in the Y direction to form the columns of the matrix, the segments lying between and defined by the upper and lower grooves forming transducer elements. The conductive layers of adjacent rows of the matrix are interconnected by suitable electrical impedances, and so are the conductive layers of adjoining columns.

To operate the device in a transmit mode, a drive source is connected to the conductive layers of selected columns and rows through suitable addressable switches to thereby select for excitation a segment of the transducer slab corresponding to and lying at the intersection of the selected row and column. The conductive layers on the selected row and column distribute the applied drive signal at reduced levels to adjacent portions of the slab through the interconnecting impedance network. The distributed signal produces a reduced drive voltage in adjacent transducer elements of the array thereby to produce a desired excitation function across the surface of the slab and thereby to provide the desired radiation wave pattern. By selecting columns or rows in sequence, the desired transmit pattern can be scanned across the transducer slab. In a receive mode of operation, the desired directivity pattern is scanned across the transducer slab by the same means, on the basis of reciprocity principles. This arrangement has the advantage of requiring fewer electrical connections while permitting accurate control of the scanning process.

In a modification of the foregoing arrangement, the transducer crystal material can be coated on its top and bottom surfaces with a resistive layer, rather than a conductive layer. The transducer elements are then formed by means of parallel traces or lines of conductive material applied in the X direction on one resistively coated surface to form the rows of the transducer matrix and in the Y direction on the opposite resistively coated surface to form the columns of the matrix. These rows and columns define segments of the transducer material which act as transducer transmitter elements upon application of a suitable drive signal. Thus, a drive signal is connected through switches to selected conductive traces, the switches serving to address the transducer columns on the opposite side. By applying a signal between a selected row trace and a selected column trace, the drive signal is applied full strength to the transducer element corresponding to and defined by the location in the slab where the row and column traces intersect. The resistive coatings on the two surfaces then cause the drive signal to be applied with decaying amplitude to transducer elements spaced away from the point of intersection to thereby produce the desired exitation function in the slab. By sequential selection of the traces, the excitation pattern can be scanned across the slab as previously described. Here again, the device operates similarly in the receive mode in accordance with reciprocity principles.

BRIEF DESCRIPTION OF THE DRAWINGS

The foregoing and additional objects, features and advantages of the present invention will be more fully understood by those of skill in the art from the following detailed description of preferred embodiments thereof taken in conjunction with the accompanying drawings, in which.

Figure 1:
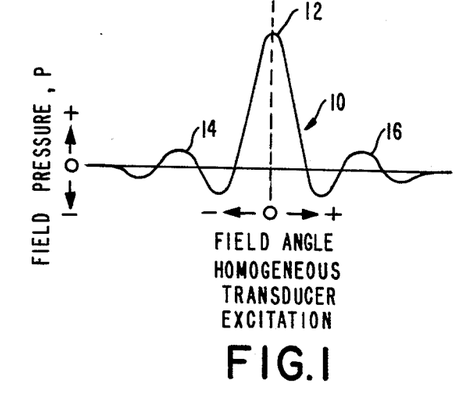
FIG. 1 is a diagrammatic illustration of a typical field pressure pattern obtained from a homogeneously vibrating transducer surface.

As has been indicated above, the problem of obtaining high resolution in an ultrasonic probe is due in large measure to the generation of side lobes in conventional transducer elements. Such side lobes are the result of the surface motion which is produced in the transducer crystal by the application of a drive voltage pulse to the transducer electrodes which are located on opposite surfaces of the crystal. The application of a constant amplitude voltage pulse over the whole transducer surface generally causes a homogeneous surface displacement motion in the crystal which in turn produces a far-field radiation pattern of the type illustrated in FIG. 1 by the curve 10. As shown, this field pattern has a main lobe of peak pressure amplitude 12 near the axis of the crystal, but the pressure amplitude decays at angles away from the axis in a non-uniform manner to produce the secondary pressure peaks 14 and 16 at some angle from the center of the crystal. These side lobes produce reflections from targets which lie in a direction differing from the supposed field of view of the transducer, thereby reducing the resolution of the desired target.

Figure 2:
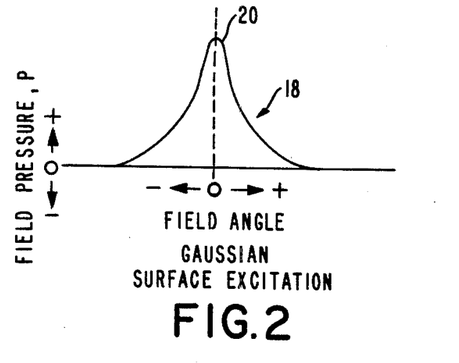
FIG. 2 is a diagrammatic illustration of a field pressure pattern obtained from a transducer surface vibrating in accordance with a Gaussian amplitude distribution.

A transducer surface resonating in accordance with a so-called bell-shaped or Gaussian displacement pattern (i.e., decaying in amplitude from a central peak amplitude as described by the exponent $-\alpha r^2$ function) exhibits a much more favorable directivity pattern particularly for biomedical imaging purposes. FIG. 2 illustrates how its pressure field pattern 18 peaks on axis and decays smoothly to zero for increasing field angles. This field pattern contains no side lobes and does not have the nearfield intensity fluctuations which are typical of other transducer sources. Such a surface motion has previously been obtained in a transducer crystal through careful selection of the geometry of the transducer crystal and/or the electrodes by which the drive signal is applied to the crystal.

Figure 3:
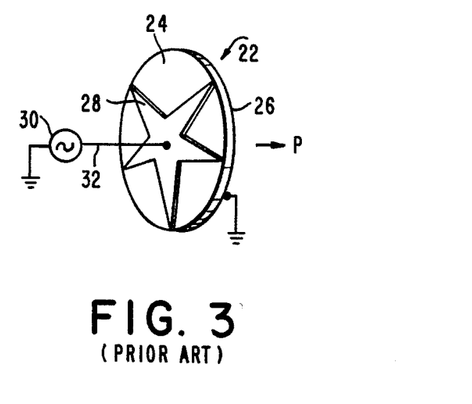
FIG. 3 is a diagrammatic illustration of a prior art transducer electrode structure designed to produce a surface excitation function of the type illustrated in FIG. 2.

An example of the geometrical approach of the prior art is illustrated in FIG. 3, wherein a transducer 22 is formed from a conventional piezoelectric crystal 24 carrying first and second electrodes 26 and 28 of silver or other suitable conductive material, plated or otherwise mounted on opposite surfaces of the crystal. Electrode 26 may be coextensive with one surface of crystal 24 and is connected to a ground reference point, while the electrode 28 on the opposite surface is shaped to concentrate the applied drive signal to the center of the crystal and is tapered, for example, in a star-shape to provide decreasing excitation toward the edges of the crystal.

The drive signal for the transducer 22 is supplied from a source 30 through a connecting line 32 which is soldered or otherwise connected to the electrode 28 at some convenient point. The shape of electrode 28 concentrates the drive voltage at the center of the transducer crystal to produce a surface motion in the crystal which has a central peak and which decays toward the edges in a function approximating the shape of curve 18 in FIG. 2. This motion produces a radiated pressure wave, indicated by the arrow P, having a relatively narrow beam with a peak amplitude at the central axis of the transducer crystal and a reduced amplitude toward the periphery of the transducer in the manner illustrated by curve 18.

As previously indicated, the generation of a desired radiated field pattern by means of geometrical features built into the transducer prevents the scanning of the generated acoustic signal across the surface of a transducer array by means of simple and easily controllable electronic scanning circuitry. Such a limitation is overcome in the present invention by the provision of a transducer array which permits the generation of a radiated field pattern of the desired shape and which also permits that field pattern to be scanned electronically across the array by simple addressable switching circuitry.

Figure 4:
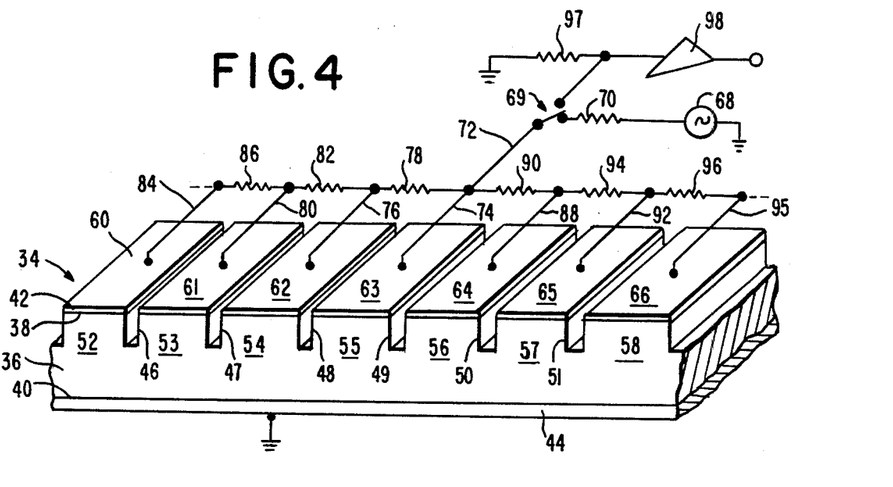
FIG. 4 is a perspective diagrammatic view of a portion of a linear transducer array constructed in accordance with the present invention.

FIG. 4 illustrates the manner in which a predetermined transducer surface motion can be produced by an applied drive signal so as to generate an acoustic wave having a preselected pattern, or function, such as the bell-shaped curve of FIG. 2. The arrangement of FIG. 4 not only permits the selection of the desired wave shape, but also can be used in a two-dimensional array to enable the wave pattern to be scanned, as will be explained. Thus, FIG. 4 illustrates a transducer device 34 which consists of a slab 36 of transducer material capable of vibrating at ultrasonic rates upon the application of a drive signal. A conventional piezoelectric substance may be used, which may be a crystalline material such as quartz crystal, a ceramic material typified by lead zirconate titanate, a piezopolymer, or other conventional material. The slab 36 is coated on its upper and lower surfaces 38 and 40 by respective layers 42 and 44 of thin conductive electrode material such as silver, gold, or the like. These electrode layers may be applied by any conventional methods such as by soldering, vacuum evaporation, plating, flame spraying, or the like.

The slab 36 is divided into segments each of which functions as a discrete transducer element by cutting a plurality of spaced, parallel grooves 46–51 across the width of the slab, the grooves extending through the upper conductive layer 42 and extending at least partway through the thickness of slab 36. These grooves divide the slab 36 and upper electrode layer 42 into separate transducer elements 52–58 each of which has electrode layer 44 in common, but has separate corresponding upper electrodes 60–66, thereby to produce a linear transducer array.

Although the transducer of FIG. 4 is illustrated with only seven (7) elements, this is for purposes of convenience in description. It will be understood that in this and in other embodiments to be described, the number of elements in the array and their interconnecting impedances extend sufficiently far from the element connected to the external transmit-receive circuitry to provide a reasonable approximation of the desired excitation function.

A source 68 of drive signals is connected through a transmit-receive switch 69 here shown in its transmit position, to a selected one of the transducer elements; for example, element 55, by connection through a resistor 70 and lines 72 and 74 to the electrode 63. Element 55 may, for example, be centrally located along the length of the transducer slab, particularly where a symmetrical function is to be produced, although other connections may be contemplated. In order to produce the desired excitation of the entire linear array, the remaining upper surface electrodes are connected through corresponding resistors to the element which is directly driven by source 68. Thus, electrode 62 is connected through line 76 and a corresponding resistor 78 to the junction of lines 72 and 74, and thus to the source 68. Electrode 61 is connected through line 80 and resistor 82 and is connected in series with resistor 78 to the junction of lines 72 and 74. Thus, supply source 68 is connected to each of the electrodes 60, 61 and 62 through one or more series-connected resistors, these resistors along with the impedances of the transducer elements 52, 53, 54 acting as a voltage divider ladder network so that the drive signal applied to each of the transducer elements 52–54 on one side of element 55 is reduced in amplitude as the distance from the center transducer element 55 increases. A similar connection is provided on the opposite side of transducer element 55 so as to provide a symmetrical excitation of transducer elements 56, 57, and 58. Thus, electrode 64 is connected by way of line 88 and resistor 90 to the junction of lines 72 and 74, electrode 65 is connected by way of line 92 and resistor 94 through resistor 90 to the same point, and electrode 66 is connected by way of line 95 and resistors 96, 94 and 90 to the junction.

In its receive mode of operation, the transmit-receive switch 69 is switched to interconnect signal line 72 with a termination resistance 97 and the received signal amplifier 98. By reciprocity, the directivity of the array in its receive mode of operation then equals its directivity in the transmit-mode of operation, if the external termination impedances in both modes of operation (70 and 97) have the same value.

Figure 5:
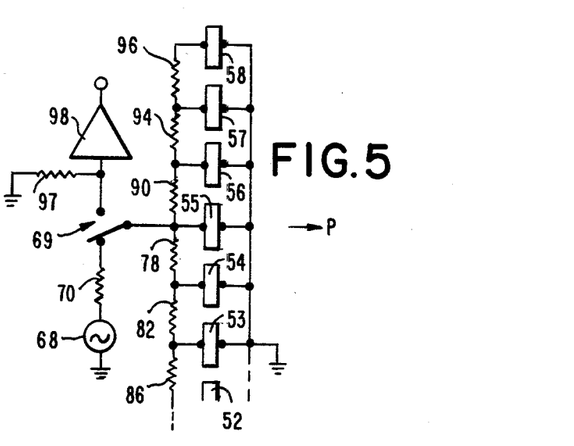
FIG. 5 is a schematic diagram of the electrical connections for the array of FIG. 4.

The electrical connections for the transducer array of FIG. 4 are illustrated in schematic form in FIG. 5. As may be seen in that figure, the resistors 78, 82 and 86 on one side of the drive source and resistors 90, 94 and 96 on the other side of the drive source distribute the voltage pulse which activates the transducer elements to the array at decreasing amplitudes, the amount of decay depending upon the value of the resistors and the impedance of the transducer elements. Thus through proper selection of the resistance values, the shape of the surface excitation function can be preselected to produce the radiated directivity pattern desired in the transmit mode of operation. Since all of the elements are excited in phase by the drive voltage, acoustic separation between elements is not required, but may be used to enhance the resonant behavior of an array. In the receive mode of operation, the interconnection network of impedances serves again to sum the received signals of all array elements with appropriate weighing factors, resulting in the same desired directivity pattern.

Although a simple series connection of resistors is shown in FIGS. 4 and 5 to connect the elements of the array, it will be understood that more elaborate means of interconnecting the elements of the array can be found without departing from the spirit of this invention. For instance, series impedances can be placed in each of the connecting lines 84, 80, 76, 74, 88, 92 and 95. Further, the array elements may be terminated to ground individually by means of impedances between ground electrode 44 and electrodes 60 through 66, respectively. Furthermore, it will be understood that although resistance elements are shown, other impedance devices such as capacitors or inductors may be used, if desired, to produce the desired excitation.

The resistive connections between the transducer elements, represented by resistors 78, 82, 86, 90, 94 and 96, can be accomplished either by discrete resistors which may be mechanically supported on a base plate or other mounting device (not shown) for the transducer array, or by a layer of resistive film overlying the conductive layer on the transducer elements, using conventional printed circuit board techniques.

Figure 6:
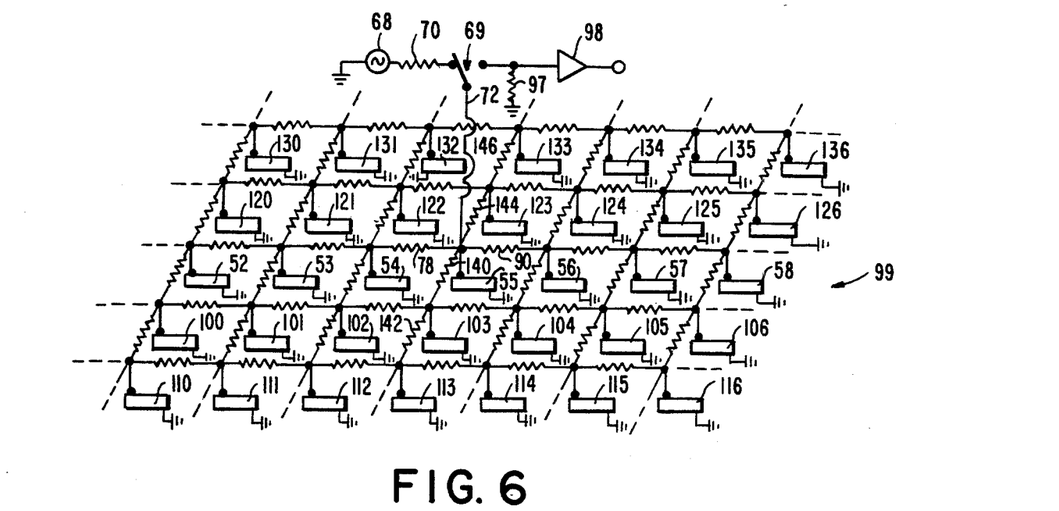
FIG. 6 is a schematic diagram of the electrical connections for a two-dimensional transducer array.

The intercoupling of the transducer elements illustrated in FIGS. 4 and 5 can be expanded from the linear transducer arrangement of those figures to a two-dimensional array 99 such as that illustrated in schematic form in FIG. 6, to which reference is now made. In the device of FIG. 6, additional transducer elements are provided which are laterally spaced from the elements illustrated in FIG. 4 and which are connected thereto through corresponding resistors. This can be accomplished by mounting a number of linear arrays in side-by-side relationship, or by cutting additional grooves in the transducer slab of FIG. 4, the additional grooves being perpendicular to grooves 46–51 and thus extending longitudinally along the slab 36 to provide side-by-side transducer elements laterally spaced across the slab. In either case, the result would be rows of transducer elements 100 through 106 and 110 through 116 (see FIG. 6) laterally spaced on one side of the centrally located row of elements 52 through 58 and rows of elements 120 through 126 and 130 through 136 laterally spaced on the opposite of the elements 52 through 58, whereby the transducer elements are arranged in rows and columns.

As illustrated in FIG. 6, all of the transducer elements in the two-dimensional array 99 are intercoupled to adjacent transducer elements in the longitudinal and lateral directions by means of a two-dimensional impedance matrix. In the preferred form, this matrix comprises the series connections of resistors illustrated in FIG. 6, wherein each transducer element is connected to its next adjacent transducer through a resistor. Thus, for example, the transducer element 55 is connected through resistor 78 to transducer element 54 and is connected to transducer element 56 through resistor 90 in the manner described with respect to FIG. 4. In similar manner, transducer element 55 is connected to elements 53 and 52 through corresponding resistors 82 and 86 and is connected to elements 57 and 58 through resistors 94 and 98, as previously described. In addition, however, element 55 is connected to elements 103 and 113 through series resistors 140 and 142 and is connected to transducer elements 123 and 133 through series resistors 144 and 146, respectively.

The matrix further includes resistors interconnecting transducer element 103 with transducer elements 102, 101 and 100 as well as with transducer elements 104, 105 and 106, includes series resistors connecting transducer element 54 to transducer elements 102 and 112 as well as to elements 122 and 132, and so on, with the resistor matrix serving to interconnect all of the adjacent elements in the longitudinal (rows) and the lateral (columns) directions.

By reason of the matrix interconnection, the drive signal from source 68 which is applied through resistor 70 and line 72 to transducer element 55 is also connected through the resistor matrix to each of the transducer elements in the two-dimensional array illustrated in FIG. 6. The applied signal thus decreases in both dimensions of the array as the distance from the element 55 increases, producing a surface excitation function that decays in accordance with the resistance values. The surface excitation of the two-dimensional array produces a radiated wave pattern that corresponds to the surface excitation function and which thus may be a three-dimensional projection of the curve 18 illustrated in FIG. 2. This arrangement gives a volumetric, rather than planar, wave pattern which can produce high resolution results in both the longitudinal and the lateral dimensions. By reciprocity, if this array is switched into its receive mode of operation, the same high longitudinal and lateral resolution is achieved.

Figure 7:
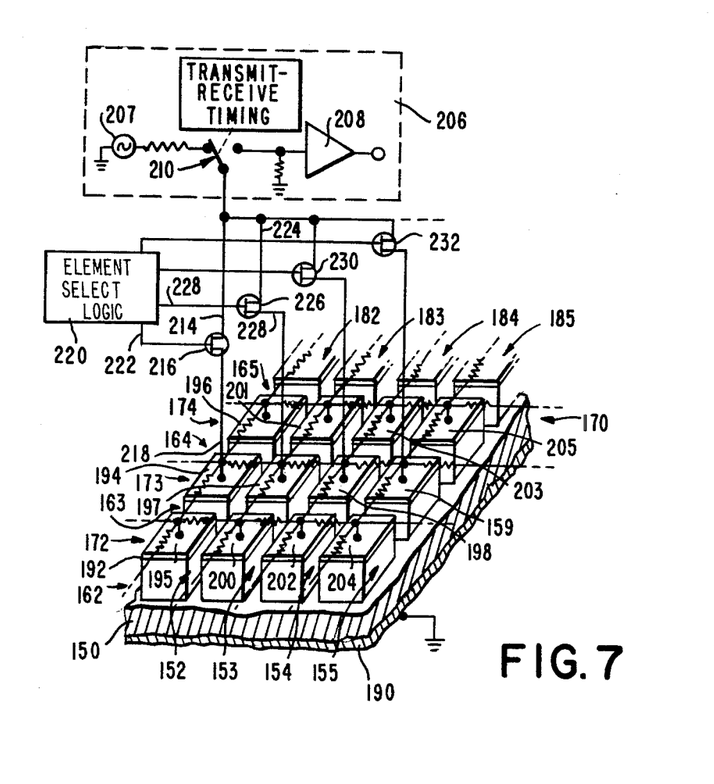
FIG. 7 is a sectional, perspective view of a two-dimensional scanning transducer array constructed in accordance with the present invention.

A two-dimensional transducer array of the type that can be used in the arrangement of FIG. 6 is diagrammatically illustrated in FIG. 7, wherein a transducer slab 150 is cut in both the longitudinal and lateral directions to form two sets of parallel spaced grooves, one set being perpendicular to the other. The grooves define an array of spaced transducer elements arranged in rows and columns generally in the manner described with respect to FIG. 6. Thus, the transducer material slab is cut by lateral grooves 152, 153, 154, 155, etc. and by longitudinal grooves 162, 163, 164, 165, etc. to form the two-dimensional array generally indicated at 170. It will be understood that only a portion of the array is shown for convenience, and that the array can be extended in either the longitudinal or transverse directions, or both, to produce an array of any desired size.

As illustrated, the grooves are formed on the top portion of the slab 150 to produce rows 172, 173, 174, etc., and columns 182, 183, 184, 185, etc., of segmented transducer elements. As was the case with the device of FIG. 4, the bottom of slab 150 is coated with a conductive layer forming a bottom electrode 190, while the top surface of the transducer slab is coated with a layer 192 which is cut by the longitudinal and lateral grooves to form individual top electrodes for each of the transducer elements forming the array. The various transducer elements so produced form a two-dimensional array, only a portion of which is illustrated in FIG. 7.

The elements of array 170 are interconnected by means of an impedance matrix, preferably a resistor matrix, which interconnects all of the adjacent transducer elements in rows and columns in the manner described with respect to FIG. 6. Thus, a first transducer element 194 is connected through resistors to its adjacent elements 195 and 196 in column 182 and is connected through series resistors to each of the transducer elements 197, 198 and 199 in row 173. Similarly, element 197 is connected through corresponding resistors to elements 200 and 201 in column 183, element 198 is connected to transducer elements 202 and 203 in column 184, and element 199 is connected through corresponding resistors to elements 204 and 205 in column 185. Transducer 195 is connected through series resistors to transducer elements 200, 202 and 204 in row 172, while transducer 196 is connected to elements 201, 203 and 205 in row 174. This pattern of row and column interconnections through corresponding resistors of the matrix continues throughout the array.

As discussed with respect to FIG. 6, the transducer array 170 of FIG. 7 could be employed with a single transmit-receive section 206 connected to one of the transducer elements to thereby provide a decaying excitation function in two dimensions across the surface of the array to provide a volumetric directivity pattern shaped in accordance with the decay pattern provided by the interconnecting resistors. However, the arrangement of FIG. 7 provides the further feature of enabling the central axis of its directivity pattern to be scanned across the array. This is accomplished by means of addressable switching circuitry which serves to connect a transmitting source 207 or a receiving amplifier 208 through transmit-receive switch 210 to the top electrodes of selected transducer elements. Thus, for example, transmit-receive section 206 can be selectively connected directly to transducer element 194 through lines 212 and 214, switching transistor 216 and line 218, with addressable switching logic 220 being connected by way of line 222 to control the operation of the switch 216. Thus, when switch 216 is turned on, and the transmit-receive switch 210 is in the transmitting mode, drive signals from source 207 are applied directly to transducer element 194 and simultaneously through the resistance matrix to the surrounding transducer elements, of which 195 through 205 are shown. Similarly, when switch 216 is turned on and the transmit-receive switch 210 is in the receive position, received signals from the bell-shaped field of directivity having its central axis at transducer element 194 is applied to the receiver amplifier 208 for further processing by the B-scan display section of the instrument (not shown).

The transmit-receive section 206 may also be connected by way of line 212 and 224 through switch 226 and line 228 directly to transducer element 197, with the operation of switch element 226 being controlled by switching logic 220 through line 228. In similar manner, switches 230 and 232 may be selected to connect the transmit-receive section to corresponding transducer elements 198 and 199, respectively, with additional connections through additional switching elements being provided as desired to shift the axis of the transducer directivity pattern from one transducer element to another. Each switch serves to connect the transmit-receive section 206 to the selected transducer element, whereby the resistance matrix interconnecting this element with the surrounding elements provides the desired vibrational characteristics of the localized area. The elements in this localized area, in turn, provide the desired directivity pattern in the transmit and receive modes of operation. The element select logic 220 allows the peak excitation to be shifted from one element to the next to thereby scan the directivity pattern across the transducer array. The element select logic 220 addresses the switches to be selected to thereby provide a desired scanning pattern and rate.

Although the arrangement of FIG. 7 operates satisfactorily, the scanning pattern available is limited by the specific connections made between the source and the individual transducer elements, thus limiting the scanning patterns available. If, for example, it should be desirable to provide scanning capabilities in both the longitudinal and lateral directions, numerous additional connections would be required, with corresponding switches and increased complexity in the switching logic. Further, in large arrays, where large numbers of resistors are required to form the matrix, the electrical circuitry becomes quite complex. A simplified structure for a scanning array is illustrated in the embodiment of FIGS. 8 and 9, to which reference is now made.

Figure 8:
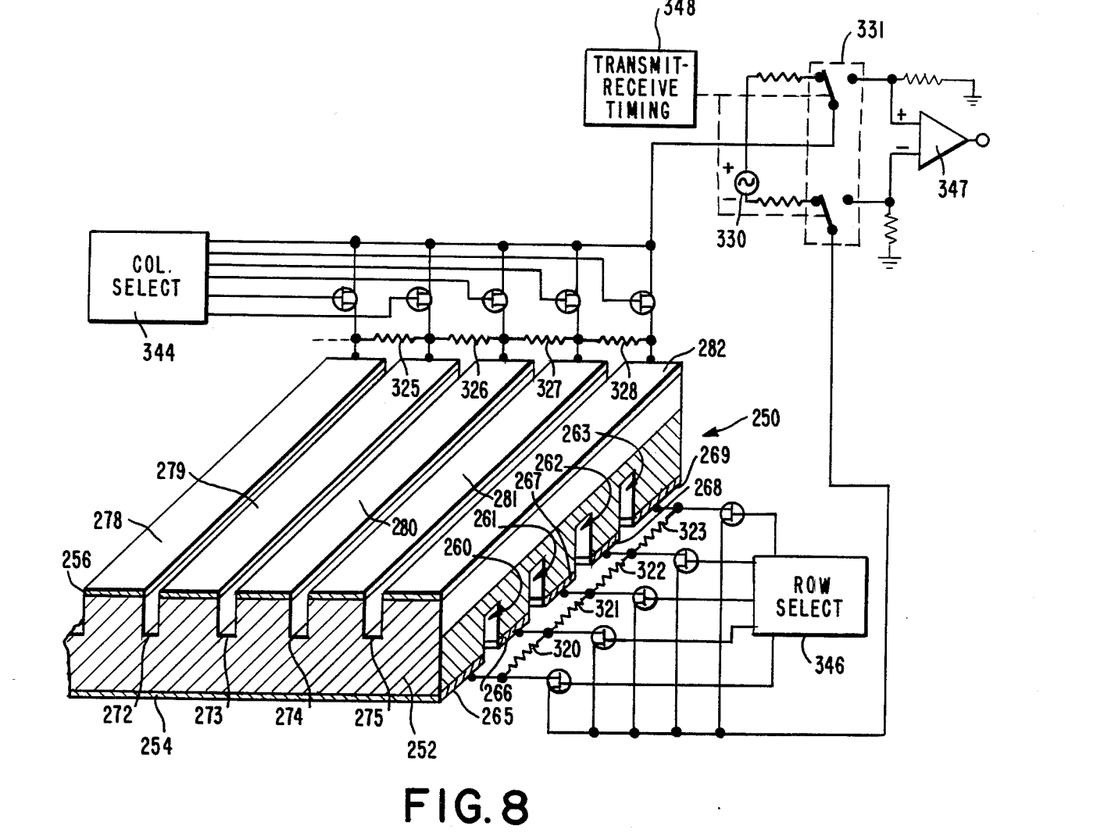
FIG. 8 is a perspective view of a modified form of the invention illustrated in FIG. 7.

The transducer array 250 of FIG. 8 is similar to that of FIG. 7 in that it comprises a slab 252 of piezoelectric material carrying bottom and top layers 254 and 256 of conductive electrode material. Again, the slab is cut by longitudinally and laterally extending grooves which divide the slab into an array of individual transducer element segments. In this case, however, the longitudinal grooves, illustrated at 260, 261, 262 and 263 are formed through the bottom surface of slab 252 and serve to divide the bottom portion of the slab into rows as well as to divide the bottom electrode material 254 into corresponding row electrodes 265 through 269. The laterally extending grooves 272 through 275 are formed through the top surface of the transducer slab, thereby dividing the top portion of the slab into columns and dividing the top electrode layer 256 into column electrodes 278 through 282. The longitudinal and lateral grooves each extend approximately half way through the slab 252 and thus define the longitudinal and lateral boundaries of transducer elements, the grooves thereby dividing the slab 252 into an array of individual transducer elements.

Figure 9:
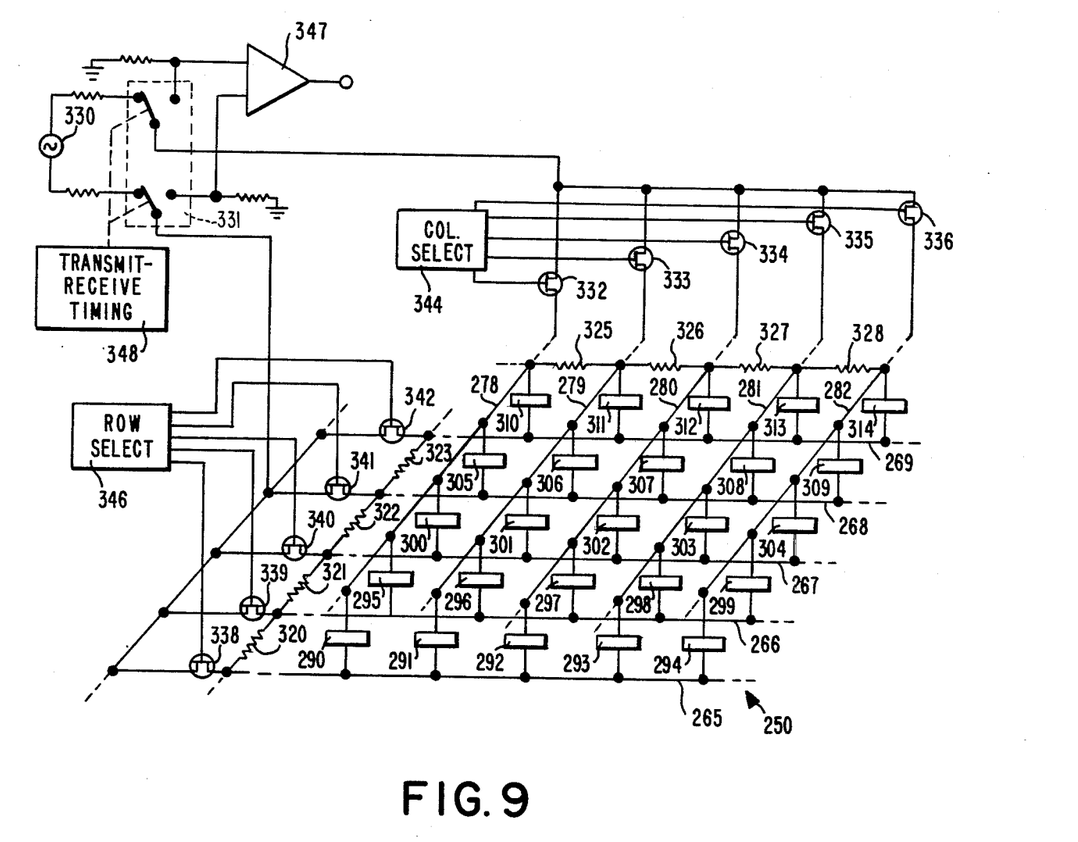
FIG. 9 is a schematic diagram of the electrical connections for the array of FIG. 8.

The transducer elements produced by the perpendicular sets of parallel spaced grooves illustrated in FIG. 8 are shown in diagrammatic form in the circuit schematic of FIG. 9. Thus, a first row of transducer segments comprises transducer elements 290 through 294, all of which are connected in common to the row electrode 265. The top portions of the transducer segments 290 through 294 are connected to the column electrodes 278 through 282, respectively, as illustrated in FIG. 9. In similar manner, a second row of transducer elements 295 through 299 are connected in common to row electrode 266 and individually to column electrodes 278 through 282, respectively. A third row of transducer elements 300 through 304 are connected to row electrode 267 and to respective column electrodes 278 through 282, a fourth row of transducer elements 305 through 309 are connected in common to row electrode 268 and to respective column electrodes 278 through 282, and the last row of transducer elements 310 through 314 are connected in common to row electrode 269 and individually to column electrodes 278 through 282. Of course, similar elements extend in all four directions of this planar array so that each of the elements shown in FIG. 8 can serve as the center of a localized area of array excitation.

In order to provide the interconnection between the various transducer elements of the array 250 to obtain the desired surface excitation of the transducer elements, the row electrodes 265 through 269 are interconnected by means of resistors 320 through 323, resistor 320 interconnecting electrodes 265 and 266, resistor 321 interconnecting electrodes 266 and 267, and so on. In similar manner, the column electrodes are interconnected by means of resistors 325 through 328, resistor 325 being connected between electrodes 278 and 279, resistor 326 being connected between electrodes 279 and 280, and so on. In this manner, all of the transducer elements are interconnected to adjacent elements in both the longitudinal and transverse directions so as to produce the desired excitation pattern. Although in the preferred form all of the resistors are equal in resistance value, it will be apparent that the resistors can be differently sized if desired. For instance, near the edges of the array one might choose a different value resistor to correct the segment drive for the fact that the array does not extend to infinity.

A source of excitation or drive voltage 330 is connected through a transmit-receive switch 331 across selected row and column electrodes in order to select for direct excitation any one of the transducer elements 290 through 314. Thus, the source 330 is connected to any selected column electrode 278 through 282 by way of controllable column switches 332 through 336 and is connected to any selected row electrode 265 through 269 by way of controllable row switches 338 through 342, respectively. Any of the switches 332 through 336 can be activated by means of an addressable column select logic circuit 344, the switches 338 through 342 can be activated by addressable row select logic circuit 346. By selecting one column select switch and one row select switch, the drive voltage from one source 330 is connected directly across the transducer element specified by the intersection of the selected electrodes to drive that element with the full source voltage. Similarly, by putting the transmit-receive switch into the receive mode, one can, by suitable setting of row and column switches, select any of the elements as the center of the receiving array directivity function and feed the received signals to receiver amplifier 347.

If the logic circuit 344 addresses column switch 333 to place the source voltage on column electrode 279, and the logic circuit 346 addresses row switch 340 to connect the opposite side of the source 330 to row electrode 267, the source voltage will be connected directly across the electrodes of transducer element 301. At the same time, the source voltage will be applied through resistor 325 to column electrode 278 and through resistors 326, 327 and 328 to column electrodes 280, 281 and 282. In similar manner, the source voltage will be applied through resistors 321 and 320 to row electrodes 266 and 265, respectively, and will at the same time be applied through resistors 322 and 323 to row electrodes 268 and 269, respectively. In this way, voltages of reduced amplitude will be applied to the transducer elements spaced away from the directly activated element 301 in the manner previously described, to produce a surface excitation on the array which approximates the curve 18 illustrated in FIG. 2 or such other excitation curve as may be desired, depending upon the value of the resistors. By advancing the selection of the column selector switches 332 through 336 and the row selector switches 338 through 342 in accordance with known addressing techniques, the location of the direction connection of the voltage source can be progressively moved across the transducer array, thereby providing an electronic scan of the surface excitation and the resulting radiated pressure wave. Here again, it will be understood that the transducer is operable in the receive mode in accordance with the reciprocity principles discussed above.

For ease of understanding, the array in FIGS. 8 and 9 is shown as driven symmetrically by a differential transmitter source 330, and terminated by a differential receiver 347 in the receive mode. This is not essential to the operation of this transducer array. The array can be driven off a current source rather than a voltage source, or the differential transmitting and receiving circuitry can be replaced by single-polarity elements referenced to ground, as shown in FIG. 7. It should also be noted that the transmit-receive switch 331 would normally be driven to shift the transducer between its two modes at a suitable rate, as by a conventional transmit-receive drive circuit 348.

Figure 10:
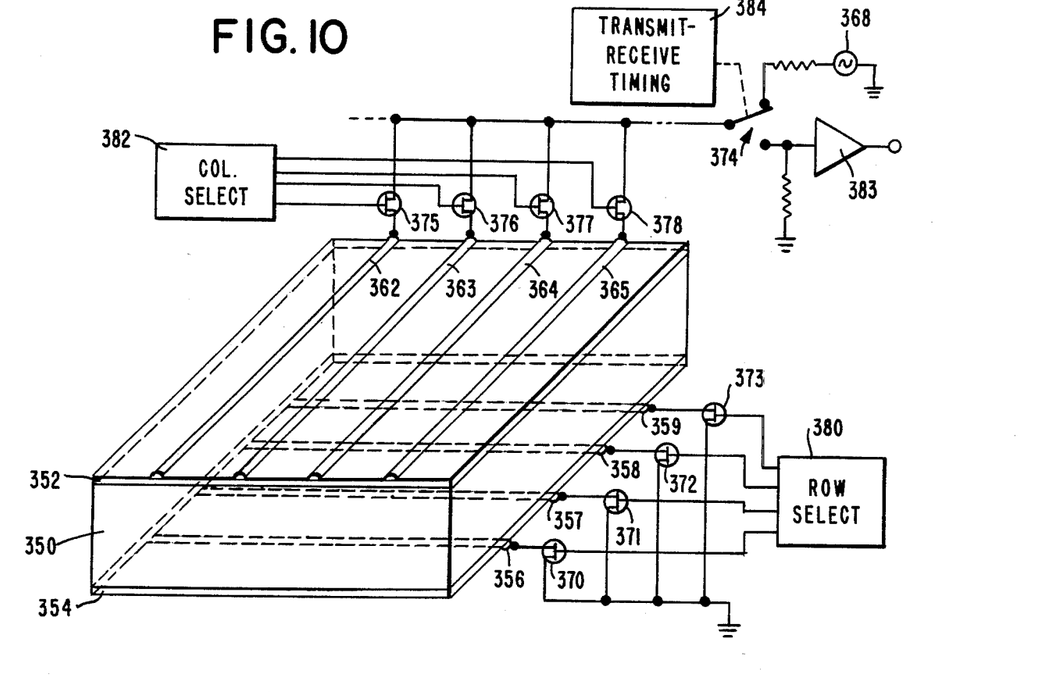
FIG. 10 is a perspective, diagrammatic illustration of a further modification of the transducer array illustrated in FIG. 7.

A variation of the scanning array of FIGS. 8 and 9 is illustrated in FIG. 10, wherein a slab of transducer material 350 carries coatings 352 and 354 on its upper and lower surfaces, respectively. In this case, however, the coatings comprise a layer of resistive film which may be plated onto the upper and lower surfaces by conventional techniques, instead of the conductive material used in prior embodiments. Rows and columns of transducer elements are defined in this embodiment by means of conductive wires, or traces, which are point-welded or glued to the resistive coating or which are plated onto the resistive material by conventional printed circuit board techniques. Thus, row segments of transducer material are defined by row connector electrodes 356 through 359 while column segments of the transducer material are defined by column electrode connectors 362 through 365, the intersections of the row and column segments defining transducer elements.

The row electrode connectors 356 through 359 are connected to one side of a drive voltage source 368 by way of row switches 370 through 373, respectively, while the column electrode connectors 362 through 365 are connected to the other side of source 368 by way of transmit-receive switch 374 through column selector switches 375 through 378, respectively. As before, addressable row select logic 380 and column select logic 382 permits activation of selected row and column switches, respectively, whereby individual transducer elements within the slab 350 and defined by the intersections of the row and column electrode connectors can be selected for direct excitation by the source 368. Similarly, the connectors can be selected for connection through transmit-receive switch 374 to a receiver amplifier 383, in the manner previously described, with the switch 374 being driven by suitable circuitry 384.

As in prior embodiments, adjacent transducer elements are electrically interconnected to the directly addressed elements by way of an impedance matrix which in this case comprises the resistive coatings 352 and 354. Accordingly, a drive signal applied to selected electrode connectors will simultaneously be applied through the resistive film to all of the other transducer elements, but at a reduced amplitude that depends on the distance from the point of application. By sequentially addressing selected row and column switches, the location of the axis of the transmit and receive directivity function of the transducer slab 350 can be progressively shifted to produce a scanning of the resulting line of view across the array.

Figure 11:
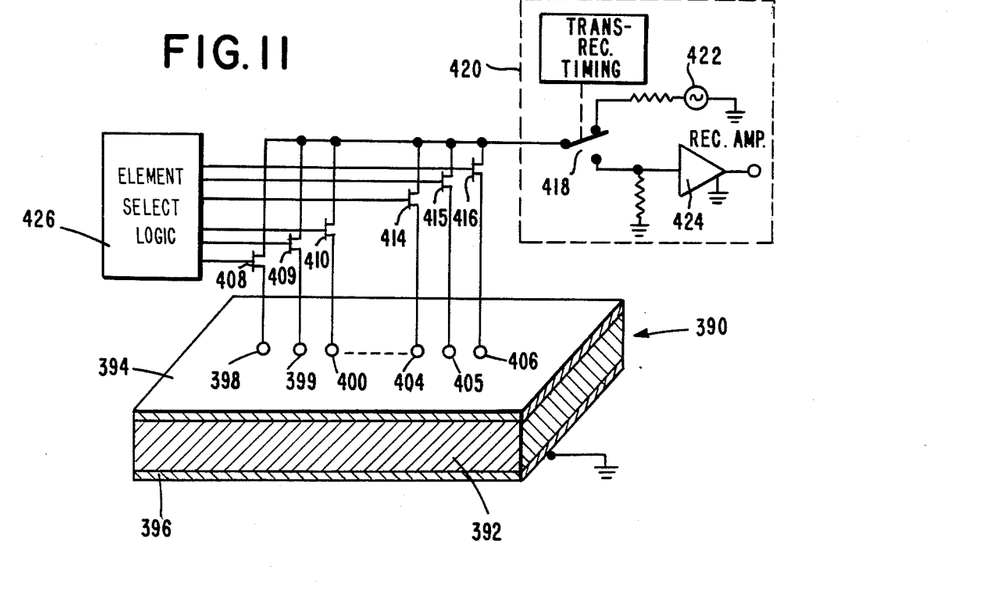
FIG. 11 is a simplified version of the array of FIG. 10.

A simplified array construction can be achieved, in the present system, if an array employing the resistive plating technology of FIG. 10 needs to be scanned only in one direction; i.e., along only one line of the array. Such a simplification is illustrated in FIG. 11, wherein a transducer element 390 is comprised of a slab of transducer matter 392 plated on its upper surface with a resistive coating 394 and on its lower surface with a conductive coating 396. A plurality of electrical connections 398, 399, 400 . . . 404, 405, 406 across the transducer 390 define a plurality of transducer elements extending between the connections and the conductive layer 396. The resistive coating in effect defines a multiplicity of adjacent transducer elements connected in rows and columns on the transducer material, the adjacent elements being interconnected through the impedance network formed by the resistive coating.

Each contact is connected through corresponding switch elements 408, 409, 410 . . . 414, 415, 416 and through a transmit-receive switch 418 in a transmit-receive section 420 to a drive source 422 or a receiver amplifier 424, in the manner described with respect to FIG. 10. Element select logic 426 activates selected switch elements 408-416 to scan the transducer elements defined by the line of electrical connections 398-406, thereby scanning the line of view of the transducer across the array of elements.

The circuitry for addressing the row and column switches of the various arrays described hereinabove may include a conventional programmed microprocessor or like control system, but such circuitry does not comprise a part of the present invention.

Thus, in order to eliminate the shortcomings of prior systems, there has been described a low cost, high resolution probe design which utilizes intercoupling of transducer elements to produce a desired transducer directivity pattern which is easily scanned across its field of view. Although the invention has been described in terms of preferred embodiments, it will be apparent to those of skill in the art that numerous variations and modifications may be made without departing from the true spirit and scope thereof as set forth in the following claims.

What is claimed is:

1. An ultrasonic transducer array exhibiting a transducer directivity pattern which is substantially symmetrical along at least one coordinate of the transducer surface, comprising:
   a source of excitation;
   a plurality of transducer elements;
   first and second excitation electrode means connected first and second opposed surfaces, respectively, of each said transducer element;
   impedance means interconnecting adjacent transducer elements; and
   means to sequentially connect said source of excitation to selected transducer elements and simultaneously through said impedance means to adjacent transducer elements to excite said selected and adjacent transducer elements to produce said directivity pattern and to scan said pattern sequentially across the transducer array by said sequential connections.

2. The transducer array of claim 1, wherein said transducer elements are formed from segments of a single plate of transducer material.

3. The transducer array of claim 2, wherein one of said first and second excitation electrode means is common to all of said transducer elements.

4. The transducer array of claim 1, wherein said impedance means comprises resistance means.

5. The transducer array of claim 1, wherein said means for connecting said source of excitation to said selected transducer elements includes transmit-receive circuitry connected to selectively operable switch means said switch means connecting said circuitry across said first and second electrode means of a selected one of said transducer elements.

6. The transducer array of claim 5, wherein said selectively operable switch means includes means for sequentially connecting said transmit-receive circuitry across a plurality of selected transducer elements to scan said array.

7. The transducer array of claim 5, wherein said impedance means comprises resistance means.

8. The transducer array of claim 7, wherein said resistance means comprises resistors connected between adjacent transducer elements.

9. The transducer array of claim 7, wherein said resistance means comprises a resistive film applied to one surface of said transducer elements, one of said first and second electrode means being connected to said film.

10. The transducer array of claim 1, wherein said transducer elements are comprised of segments of a single slab of transducer material.

11. The transducer array of claim 10, wherein said slab is grooved to define said segments.

12. The transducer array of claim 10, further including first and second sets of parallel grooves formed in said slab of transducer material, said first set of grooves being angled with respect to said second set of grooves to define a two-dimensional array.

13. The transducer array of claim 12, wherein said first and second sets of grooves are formed on the same surface of said transducer material.

14. The transducer array of claim 13, wherein said grooves are cut through one of said first and second excitation electrode means, whereby the cut electrode means is divided into a plurality of electrodes, one for each transducer element.

15. The transducer array of claim 12, wherein said first and second sets of grooves are formed on opposite surfaces of said transducer material.

16. The transducer array of claim 15, wherein said first set of grooves are cut through a first one of said excitation electrode means and said second set of grooves are cut through a second one of said excitation electrode means to form row and column electrodes, respectively, on opposite sides of said transducer slab.

17. The transducer array of claim 16, wherein said means to connect said source of excitation to said selected transducer elements includes row and column selectively operable switch means, said switch means connecting said source of excitation across selected row and column electrodes, whereby selection of a row electrode switch means and a column electrode switch means will connect said source of excitation across a specified transducer element.

18. The transducer array of claim 17, further including addressable logic means for activating said selectively operable switch means in a sequential manner to connect said source of excitation sequentially to selected transducer elements, thereby to scan said array.

19. The transducer array of claim 12, wherein said means to connect said source of excitation to said selected transducer elements includes transmit-receive circuitry connected to selectively operable switch means, said switch means connecting said circuitry across said first and second electrode means of a selected one of said transducer elements.

20. The transducer array of claim 10, wherein said impedance means comprises resistive layers coated on opposite surfaces of said transducer slab, and wherein said first excitation electrode means comprise spaced, parallel conductive traces connected to the resistive layer on a first surface of said slab, and wherein said second excitation electrode means comprise spaced, parallel, conductive traces connected to the resistive layer on a second surface of said slab.

21. The transducer of claim 20, wherein said second conductive traces are angled with respect to said first conductive traces.

22. The transducer array of claim 1, wherein
said plurality of transducer elements are segments of a single slab of transducer material;
said first electrode means comprises a continuous resistive coating on one surface of said slab;
said means to connect transducer elements to electronic circuitry comprises a plurality of spaced connection points on said resistive coating to define said transducer segments; and
means for connecting the transmit-receive circuitry to a selected one of said connection points.

23. The transducer array of claim 1, wherein said impedance means electrically couples adjacent transducer elements whereby a signal applied to one said transducer element is applied at reduced amplitude to adjacent transducer elements.

24. The transducer array of claim 1, further including means in the transmit-receive circuitry for supplying a drive signal to said at least one of said transducer elements, said drive signal being coupled to adjacent transducer elements at reduced amplitudes through said impedance means, whereby the directivity of said array is determined by said impedance means.

25. The transducer array of claim 24, wherein said means to connect at least one of said transducer elements to transmit-receive circuitry includes switch means for sequentially connecting said drive signal to selected transducer elements to scan said array.

26. The transducer array of claim 25, wherein said impedance means electrically couples adjacent transducer elements whereby said drive signal applied to a selected transducer element is also applied through said impedance means to adjacent transducer elements at reduced amplitude.

27. The transducer array of claim 1, wherein said means to sequentially connect said source of excitation to selected transducer elements comprises selectively operable switching circuit means.

28. The transducer array of claim 27, wherein said means to sequentially connect said source of excitation to selected transducers includes transmit-receive circuitry.

29. The transducer array of claim 1, wherein said impedance means is selected to produce a pattern of excitation of said transducer elements which corresponds to said directivity pattern.

30. An ultrasonic transducer array exhibiting a transducer directivity pattern of predetermined form, comprising:
a plate of transducer material having an upper surface and a lower surface;
a resistive coating on said upper surface;
a conductive coating on said lower surface;
a plurality of electrical connector locations spaced across said resistive coating to define a plurality of transducer elements forming an array;
transmit-receive circuitry for selectively exciting said transducer array and for receiving signals applied to said array; and
means for connecting said transmit-receive circuitry directly to the transducer element of at least one of said connector locations, said resistive coating connecting said circuitry to the remaining elements in said array.

31. The transducer of claim 30, said means for connecting further including means for selectively connecting said transmit-receive circuitry to said connector locations, whereby said transducer directivity pattern is selectively located with respect to said array.

32. The transducer of claim 30, said means for connecting further including means for sequentially connecting said transmit-receive circuitry to said connector locations to scan said transducer directivity pattern across said array.

33. The transducer of claim 30, wherein said means for connecting comprises switching means.

* * * * *